United States Patent [19]

Borrows

[11] 4,341,997
[45] Jul. 27, 1982

[54] MAGNETIC PARTICLE INSPECTION PROCESS USEABLE WITH SIMULTANEOUS ILLUMINATION BY ULTRA-VIOLET AND WHITE LIGHT

[75] Inventor: Kenneth P. Borrows, Schaumburg, Ill.

[73] Assignee: Magnaflux Corporation, Chicago, Ill.

[21] Appl. No.: 94,764

[22] Filed: Nov. 14, 1979

[51] Int. Cl.³ .................... G01R 33/00; G01N 27/84
[52] U.S. Cl. ..................................... 324/215; 324/216
[58] Field of Search .............................. 324/214–216; 252/62.52; 250/341

[56] References Cited

U.S. PATENT DOCUMENTS 3,402,349  9/1968  Parker .................................. 324/215
3,485,758  12/1969  Borucki et al. ................... 252/62.52
3,609,532  9/1971  Van Kirk et al. .................... 324/215

FOREIGN PATENT DOCUMENTS 1154462  6/1969  United Kingdom .
1289727  9/1972  United Kingdom .
1527745  10/1978  United Kingdom .

Primary Examiner—Gerard R. Strecker
Assistant Examiner—Walter E. Snow
Attorney, Agent, or Firm—Hill, Van Santen, Steadman, Chiara & Simpson

[57] ABSTRACT

A method and composition for non-destructive testing of a magnetizable workpiece in which the surface of the workpiece is coated with a composition containing discrete magnetic particles consisting of a ferromagnetic particle core, fluorescent pigment particles attached to said core and a cascading opacifier combined therewith, preferably by means of a film-forming encapsulating resin. The particles of the daylight fluorescent pigment are sufficiently large so that they fluoresce with sufficient intensity to be seen in normal lighting conditions. Consequently, the magnetizable pieces to be inspected can be simultaneously inspected under ultra-violet and white light excitation to reveal both fine cracks and large voids.

5 Claims, No Drawings

MAGNETIC PARTICLE INSPECTION PROCESS USEABLE WITH SIMULTANEOUS ILLUMINATION BY ULTRA-VIOLET AND WHITE LIGHT

BACKGROUND OF THE INVENTION

1. Field of the Invention

This invention is in the field of non-destructive testing utilizing fluorescent magnetic particles, the particles including a daylight fluorescent pigment and a cascading opacifier attached to a ferromagnetic particle core of such size that the particles can be used for magnetic inspection processes under simultaneous illumination by ultra-violet light and white light.

2. Description of the Prior Art

Magnetic particles have been used for flaw detection in magnetizable workpieces for many decades. More recently, the magnetic particles have been combined with fluorescent particles either in the form of a water or oil suspension whereupon the workpiece was inspected under filtered ultra-violet or black light to observe any concentration pattern of fluorescent particles caused by a surface discontinuity. Prior art patents referring to this type of inspection technique include Switzer U.S. Pat. No. 2,267,999 and Kazenas U.S. Pat. No. 3,936,287. These patents relate, respectively, to lacquer bonded and resin bonded fluorescent magnetic particles for use in this type of inspection process.

Methods of making fluorescent coated magnetic particles have also been described in my previous U.S. Pat. No. 3,404,093 and in U.S. Pat. No. 3,485,758 in which James S. Borucki was a co-applicant.

One of the principal areas of application of the fluorescent magnetic particle inspection process is that of steel billet inspection. In this type of inspection, the billet is inspected for longitudinal seams, and the fluorescent magnetic particle inspection takes place under black light in a darkened inspection area. Many billets, however, contain corner tears or other imperfections that because of their large size or orientation to the magnetic field do not produce indications, and cannot be seen in the dark. Consequently, the location of such imperfections has required a separate inspection in visible light.

SUMMARY OF THE INVENTION

The present invention provides a method and composition for the non-destructive testing of magnetizable workpieces under conditions in which small and large imperfections can be located simultaneously. The method consists of applying to the surface of the workpiece discrete magnetic particles having a ferromagnetic particle core, fluorescent pigment particles attached to said core and a cascading opacifier associated with the core, the fluorescent pigment particles being at least 2 microns in maximum dimension, creating a magnetic field along said workpiece so that the particles are attracted to imperfections therein, and inspecting the workpiece for imperfections while simultaneously illuminating the workpiece with separate sources of ultra-violet and white light. In a particularly preferred form of the invention, the cascading opacifier is fluoranthene, and the core particles have a maximum dimension of from 25 to 150 microns (500 to 100 U.S. Standard mesh). The core particles and daylight fluorescent pigment particles are held together by means of encapsulation with a film-forming resin, which also serves as the carrier for the opacifier.

DESCRIPTION OF THE PREFERRED EMBODIMENTS

In accordance with the present invention, I provide a fluorescent composition for magnetic particle inspection including ferromagnetic core particles preferably of a size ranging from 25 to 150 microns (500 to 100 U.S. Standard mesh) in maximum dimension and daylight fluorescent pigment particles attached to the core. The particles can be suitably attached to the core by encapsulation with a film-forming resin such as a polyamide resin, which most preferably contains a cascading opacifier. The fluorescent dye particles have a maximum dimension of at least 2 microns, and may range from about 2 to 10 microns in maximum dimension. The maximum dimension of the ferromagnetic core particles is at least as great as the maximum dimension of the fluorescent pigment particles, and is preferably at least twice as large.

Inspection with fluorescent magnetic particles is normally performed in a darkened area, as the indications are usually not bright enough to be seen easily when more than 2 to 5 foot-lamberts of visible light is present. In addition to the inconvenience to inspectors of having to work in an isolated, darkened area, the inspection method fails to find large voids of the sort which do not cause indications to form such, for example, as corner tears and other large voids in the surfaces of steel billets.

The present invention provides a fluorescent magnetic particle that is so bright that it can easily be seen when a minimum of 10 to 15 foot-lamberts of visible light is present on the test surface. With such illumination, large voids can easily be seen, and the need for a separate visual inspection after ultra-violet inspection is eliminated.

The larger core particles allow for a much thicker layer of fluorescent pigment to be attached to the surface, and consequently produce a fluorescent response which is four to fives times as intense as the fluorescent response obtained from a typical powder produced according to U.S. Pat. No. 3,485,758 which utilizes very fine powders on the order of $\frac{1}{2}$ micron or less.

The increase in brightness of the fluorescent materials can only be classified as unexpected. I can, however, offer a possible explanation for this unexpectedly higher fluorescent brightness. It is a well-known phenomenon in the technology of liquid fluorescent penetrants that very thin layers of penetrant liquid are only dimly fluorescent. Since only the black light that is absorbed by the material is available to cause fluorescence, very thin layers do not fluoresce with as much intensity as thicker layers because they are not thick enough to absorb all of the radiation. Very small particles of the type described in U.S. Pat. No. 3,485,758 contain even smaller pigment particles and it may be possible that these tiny particles are also too small to absorb all of the incident radiation and so fluoresce at less than full strength.

Furthermore, it is not practical to coat magnetic particles of about 5 microns in dimension with 10 micron pigment particles. Attempts to do this result in the finer magnetic particles coating the pigment and hiding its fluorescence. This problem is not present in the present invention where relatively large ferromagnetic core particles are used, and are easily and thoroughly coated with relatively large fluorescent pigment particles.

The particles produced according to the present invention are much brighter, as noted previously. When irradiated by 365 nm ultra-violet irradiation at an intensity of 1000 microwatts/cm$^2$, the particles of the present invention fluoresce with a brightness of 20 to 25 foot-lamberts, as opposed to 6 to 7 foot-lamberts for conventional fluorescent magnetic particles. This high brightness level permits inspection at an ambient white light level of 20 to 25 foot-lamberts. At this light intensity, fluorescent indications of conventional fluorescent magnetic particles are simply not visible.

The composition of the present invention also makes use of a cascading opacifier of which by far the most important example is fluoranthene. Such opacifiers are not normally termed fluorescent dyes but exhibit the property of absorption of rays in the ultra-violet region with the emission of additional visible light over and above what would be reflected if the substance were submitted to visible light radiation only. In addition to fluoranthene, it is possible to use opacifiers such as multi-ring benzenoid hydrocarbons such as anthracene and pyrene, as well as fused polycyclic hydrocarbons such as pentalene and ovalene.

Commercially available daylight fluorescent pigments are designed to be activated primarily by visible light. Typically such pigments may contain a yellow dye activated most efficiently by 425–450 nm light and a red dye activated most efficiently by light at 550 nm. While both dyes are also activated by black light, their absorption coefficients are typically very much lower at 365 nm than at their absorption peaks. The incorporation of the cascading opacifier is helpful because it strongly absorbs light at 365 nm and cascades at to about 440 nm even though it is merely dissolved in the encapsulating binding resin matrix.

Suitable magnetic core materials include iron particles, carbonyl iron, iron oxides such as gamma $Fe_2O_3$, natural and synthetic magnetite, $Fe_3O_4$, mixtures thereof, and ferrites.

The daylight fluorescent materials are resins which are commercially available and fluoresce various colors. One material which I have used satisfactorily is "Lawter B3515 Gold Yellow" which fluoresces in daylight to a gold-yellow color. Other daylight fluorescent resins, however, can also be used but some are somewhat more difficult to handle in manufacture.

The fluorescent particles according to the present invention can be made by the process described in the aforementioned U.S. Pat. No. 3,485,758. Basically, the magnetic and fluorescent pigment powders and opacifier are mixed in liquid suspension in a blender or colloid mill under sufficiently high shear to effect a cohesion between the various particles due to the operation of Van der Wall forces. In general, the blade of the blender or the rotor of the colloid mill are driven so as to rotate at a speed of at least 5400 and up to 7500 or even 12,000 r.p.m. Under the resulting shear due to high collision forces, the fluorescent pigment particles are caused to adhere directly to the larger magnetic particles.

As far as encapsulation is concerned, I prefer to use a relatively long chain linear polyamide derived from the reaction of dimerized linoleic acid with diamines or other polyamines of the general formula:

HO(—OC—R—CONHR'—NH—)$_n$H where R is a hydrocarbon group of indeterminate configuration containing about 34 carbon atoms, R' is —CH$_2$CH$_2$— and n is an integer of at least 2.

The polyamine generally used in the manufacture of polyamide resins is ethylene diamine. Blends of polyamide resins having a melting point of about 100° C. can also be used. The preferred polyamide resins having molecular weights averaging between 6000 and 9000 are thermoplastic. They have sharp melting points between 105° and 115° C. and are soluble in water-miscible, relatively volatile, aliphatic organic solvents, such as lower alcohols containing 1 to 5 carbon atoms per molecule, in methyl ethyl ketone, acetone, and mixtures thereof.

In the use of the polyamide resins, the resins are dissolved in isopropanol or other water-miscible volatile organic solvents. The premixed magnetic powder, fluorescent pigments, and opacifier are then added slowly to the resulting solution to form a slurry.

The addition of water in sufficient amount to the slurry causes the separation of discrete aggregates comprising cores of mixed magnetic and fluorescent pigment particles, encapsulated by the resin containing the opacifier as an adherent coating thereover. Apparently, the polyamide resins upon dilution of the solvent with water acquire a negative electrostatic charge whereas the magnetic particles have a positive charge. Because of the opposite charges on the particles, there is a tendency of the particles to be pulled together under the forces acting upon them and to adhere to each other.

The following tables list both the broad and the preferred ranges of composition for the fluorescent magnetic particles of the present invention, their percentages being percentages by weight:

| Ingredient | Broad | Preferred |
|---|---|---|
| Magnetic core particles | 70–90% | 75–85% |
| Fluorescent pigment particles | 3–20% | 7–15% |
| Fluoranthene | up to 1% | 0.1–1% |
| Encapsulating resin | 1–10% | 5–9% |

A particularly preferred composition is given in the following table:

| | |
|---|---|
| Iron powder | 81% |
| "Unirez" (polyamide resin) | 7% |
| "Lawter B3515 Gold Yellow" | 11.5% |
| Fluoranthene | 0.5% |

In use, the encapsulated compositions of the present invention are suspended in a water bath or in an oil suspending liquid, but water is preferred because it reduces the cost and eliminates any bath flammability. The fluorescent magnetic particles can be marketed in a concentrated form which includes wetting agents, dispersing agents, rust inhibitors, and antifoam agents.

The proportion of magnetic particles in the bath must be maintained at a uniform level. If the concentration varies, the strength of indication also varies, and indications may be misinterpreted. Fine indications may be missed entirely with a weak bath. Too heavy a concentration of particles gives a confusing background and excessive adherence of particles at external poles, thus interfering with clean-cut indications of extremely fine discontinuities.

It should be evident that various modifications can be made to the described embodiments without departing from the scope of the present invention.

I claim as my invention:

1. A method of non-destructive testing of a magnetizable workpiece which comprises:

applying to the surface of said workpiece discrete magnetic particles having a ferromagnetic particle core, fluorescent pigment particles physically attached to said core and a cascading opacifier, said fluorescent pigment particles being at least 10 microns in maximum dimension, said magnetic core particles having a maximum dimension at least twice as large as the maximum dimension of said fluorescent pigment particles, creating a magnetic field along said workpiece so that the particles are attracted to imperfections therein, and inspecting said workpiece for imperfections while simultaneously illuminating said workpiece with separate sources of ultra-violet and white light, said magnetic particles having the property of fluorescing with a brightness of at least 20 foot-lamberts when irradiated with 365 nm ultra-violet light at an intensity of 1000 microwatts/cm$^2$, the ambient white light level being at least 10 foot-lamberts.

2. A method according to claim 1 in which said opacifier is fluoranthene.

3. A method according to claim 1 in which: said core particles have a maximum dimension of from 25 to 150 microns.

4. A method according to claim 1 in which: said fluorescent pigment particles have a maximum dimension of from 10 to 50 microns.

5. A method according to claim 1 in which: said magnetic particles, said opacifier and said fluorescent pigment particles are encapsulated in a film-forming resin.

* * * * *